United States Patent [19]
James

[11] Patent Number: 6,021,348
[45] Date of Patent: Feb. 1, 2000

[54] STIMULATION AND HEATING DEVICE

[76] Inventor: Brian C. James, 880 Siesta Dr., Sarasota, Fla. 34236

[21] Appl. No.: 09/007,861

[22] Filed: Jan. 15, 1998

Related U.S. Application Data

[60] Provisional application No. 60/053,574, Jul. 24, 1997.

[51] Int. Cl.[7] ..................................................... A61N 1/04
[52] U.S. Cl. ................................ 607/3; 607/96; 607/115; 607/152
[58] Field of Search .................................. 607/3, 46, 96, 607/90, 99, 115, 148, 149, 152

[56] References Cited

U.S. PATENT DOCUMENTS

| | | |
|---|---|---|
| 940,151 | 11/1909 | Heath . |
| 5,097,828 | 3/1992 | Deutsch . |
| 5,336,255 | 8/1994 | Kanare et al. . |
| 5,601,618 | 2/1997 | James . |
| 5,674,261 | 10/1997 | Smith ........................................ 607/148 |

*Primary Examiner*—William E. Kamm
*Assistant Examiner*—George R. Evanisko
*Attorney, Agent, or Firm*—Charles J. Prescott

[57] ABSTRACT

A combination soft body tissue stimulator and heating device including two thin, flat, multi-layered flexible pads, each formed as a unit, one side of which defines a working surface. The working surface of each pad is defined by a very thin conductive foil layer which, when properly installed, makes electrical contact with, and receives support from, a separate disposable double-sided flexible adhesive electrode attached to the skin over the soft tissue. The electrodes adhesively attached to the skin are generally aligned with the conductive working surface so that only the adhesive attachment between each working surface and one electrode is required to hold each pad in place against the skin. A resistive heating element is layered within the pad which is generally coextensive with and electrically isolated from the working surface. A thin layer of foam or neoprene is attached against the other surface of the heating element or layer. Each conductive working surface and each heating element of each pad are connectable to a pulsed electrical current and to a d.c. battery supply, respectively, for simultaneous stimulation and heating of any desired soft body tissue area. The working surface of one pad serves as a positive terminal, while the other serves as a ground or negative terminal for electrical current transfer through body tissue.

6 Claims, 5 Drawing Sheets

STIMULATION AND HEATING DEVICE

This application claims the benefit of U.S. Provisional application Ser. No. 60/053,594 filed Jul. 24, 1997.

BACKGROUND OF THE INVENTION

1. Scope of Invention

This invention relates generally to therapeutic devices for treating distressed soft body tissue and more particularly to a device for therapeutic electrical stimulation and simultaneously heating of soft body tissue.

2. Prior Art

Therapeutic electrical stimulation of soft body tissue is well known. These devices which produce transcutaneous electrical nerve stimulation are known as TENS devices and are used to both relieve chronic pain and to produce muscle building stimulation. It is also well known to treat injured and weakened soft body tissue through the use of the topical application of heating atop the body tissue to be treated.

Many devices beginning with the earliest of the resistive wire heating pads are well known in prior art to accomplish the individual function of heating. The more recently developed TENS units are well known for therapeutic electrical stimulation of muscles and soft body tissue. A more complex therapeutic device for providing heating or cooling of the skin and underlying body tissue is disclosed in U.S. Pat. No. 5,097,828 invented by Deutsch. This device includes a handle and a thermally conductive head which utilizes Peltier effect devices for heating or cooling a contact plate within the head. The contact plate may also be connected to a high-voltage source for electrical stimulation.

In U.S. Pat. No. 5,336,255, Kanare et al. have disclosed an electrical stimulation and heating or cooling pack which includes a non-conductive pouch and straps for positioning and holding the pouch against a body part. Flexible conductive patches attached to the pouch are connectable to a remote pulse generator. An electrically conductive adhesive gel pad is also provided for coupling the conductive patch to the body part. By this arrangement, both heating or cooling and electrical stimulation of a body part are provided.

Heath, in U.S. Pat. No. 1,377,158, teaches an electrical resistance unit which can adapt to many uses, including heating devices. My previous U.S. Pat. No. 5,601,618 discloses a very simple device for providing combination electrical stimulation or TENS-type soft body tissue stimulation and the simultaneous heating of the body tissue. The device is hermetically sealed by molding into a single unit and is extremely compact and portable, relying upon low current dry battery power for heating and the utilization of double-sided adhesive conductive electrodes which adhesively attach to the skin area over the soft body tissue for supporting the device against the skin during use.

The present invention improves upon my previous '618 patent by increasing compactness and manufacturing simplicity and by providing matched pairs of stimulating and heating pads, each of which are individually placeable in any desired spacing, but are electrically dependent upon one another and body tissue therebetween for neuromuscular stimulation. An electrical cable includes a Y-splitter which extends from a main cable which may be utilized to limit the operable spaced between the pads of each pair of pads.

BRIEF SUMMARY OF THE INVENTION

This invention is directed to a combination soft body tissue stimulator and heating device including two thin, flat, multi-layered flexible unitary pads each formed as a unit, one side of which defines a working surface. The working surface of each pad is defined by a very thin conductive foil layer which, when properly installed, makes electrical contact with, and receives support from, a separate disposable double-sided flexible adhesive electrode attached to the skin over the soft tissue. The electrodes adhesively attached to the skin are generally aligned with the conductive working surface so that only the adhesive attachment between each working surface and one electrode is required to hold each pad in place against the skin. A resistive heating element is layered or sandwiched within the pad and is generally coextensive with and electrically isolated from the working surface. A thin foam elastomer layer covers the heating element and forms the opposite outer surface from the working surface of each pad. Each conductive working surface and the heating element are separately connectable to a pulsed electrical current and a d.c. battery supply, respectively, for simultaneous stimulation and heating of any desired soft body tissue area. The working surface of one pad serves as a positive terminal, while the other serves as a ground or negative terminal for electrical current transfer through body tissue.

It is therefore an object of this invention to provide an improved portable, compact device for the simultaneous therapeutic electrical stimulation and heating of soft body tissue.

It is another object of this invention to provide a device for therapeutic electrical stimulation and simultaneous heating of soft body tissue which is adhesively connectable to the skin and held in place by double-sided adhesive electrodes only.

It is yet another object of this invention to provide a device for therapeutic electrical stimulation and simultaneous heating of soft body tissue which is hermetically sealed, extremely compact and portable and utilizes independent low levels of voltage electrically isolated one from another for both therapeutic functions.

It is still another object of this invention to provide a flexible device for the therapeutic electrical stimulation and simultaneous heating of virtually any portion of soft body tissue.

In accordance with these and other objects which will become apparent hereinafter, the instant invention will now be described with reference to the accompanying drawings.

DETAILED DESCRIPTION OF THE INVENTION

Figure 1A:
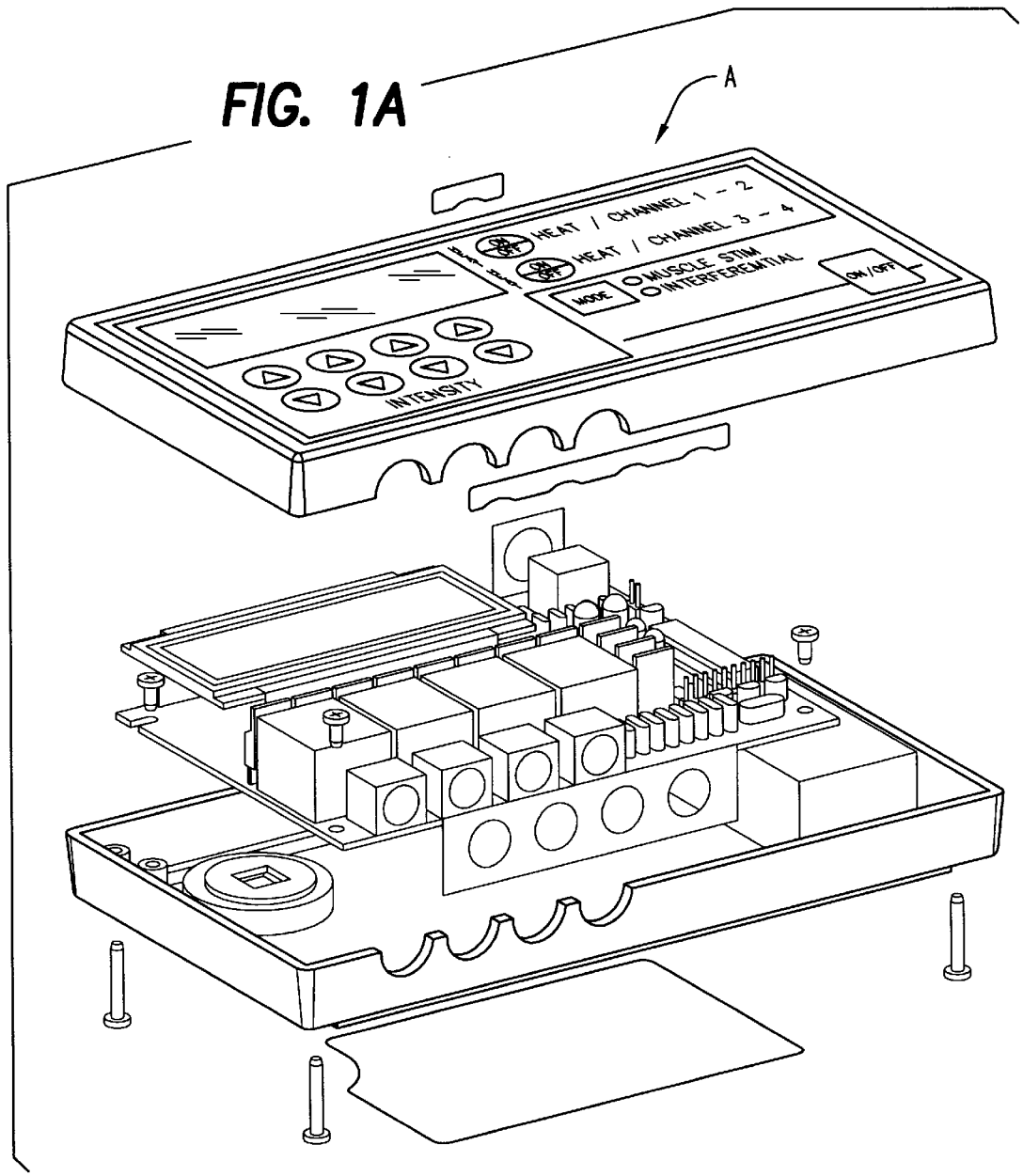
FIG. 1A is an exploded view of a control module for interconnection and use of the invention.
Figure 1B:
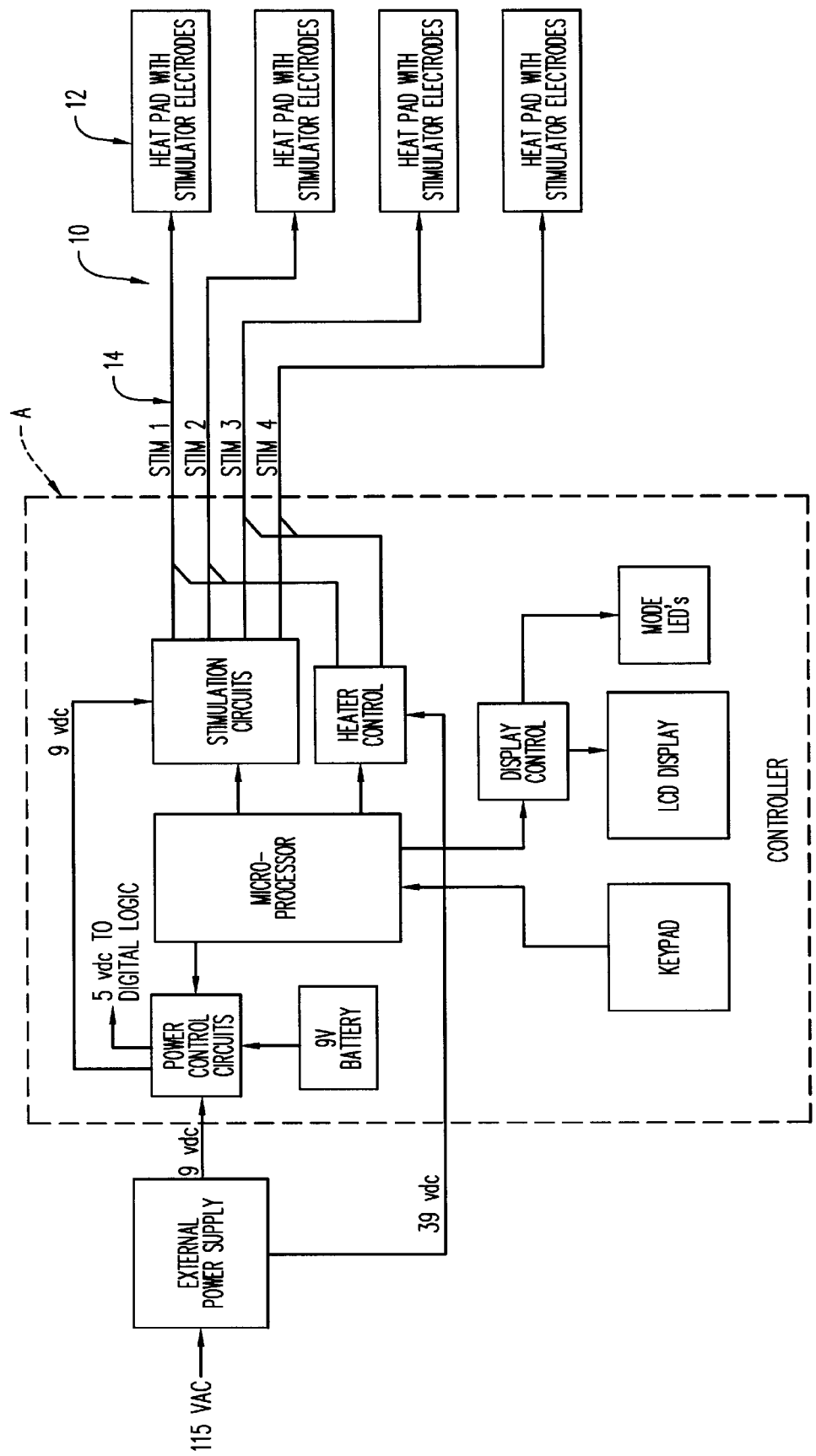
FIG. 1B is a block diagram of the control module and externally connected stimulation pads.
Figure 2:
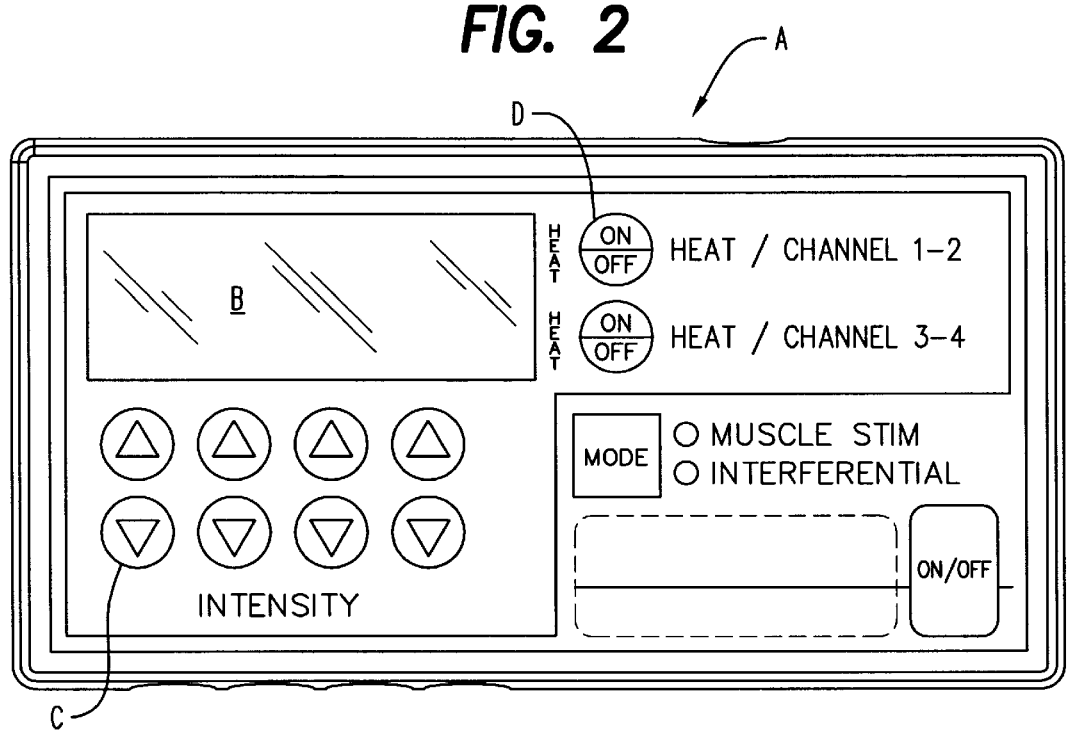
FIG. 2 is a top plan view of FIG. 1.
Figure 3:
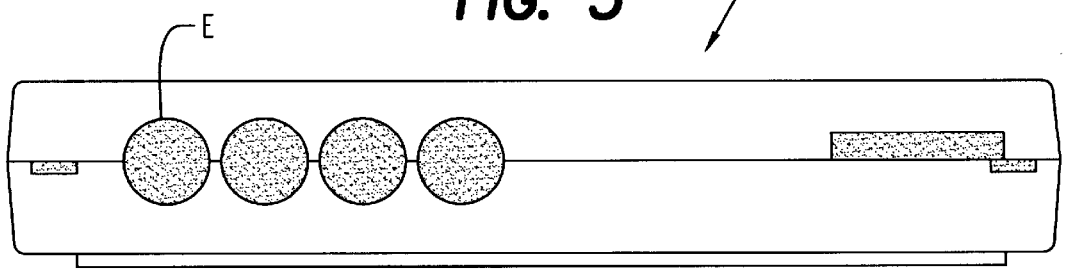
FIG. 3 is a front elevation view of FIG. 2.

Referring now to the drawings, a control module for use in powering and controlling the present invention during operation is shown generally at letter A in FIGS. 1A, 1B, 2 and 3. The control module A includes a display panel which provides a visual representation of whether the heat element is being simultaneously used with one of the two selections of soft tissue stimulation, namely, "muscle stem", or "interferential" electrical muscle stimulation. Intensity of each of the four output channels E of muscle stimulation and heat level is controlled by control pads shown typically at C. The details of the control circuitry within this control module A are shown in FIG. 1A. The structural support features of the module, some of which are shown in the exploded view of FIG. 1, are well within the scope of ordinary skill in the art of designing and constructing such a module and electrical circuit of FIG. 1B and do not form an essential component of this invention.

Figure 4:
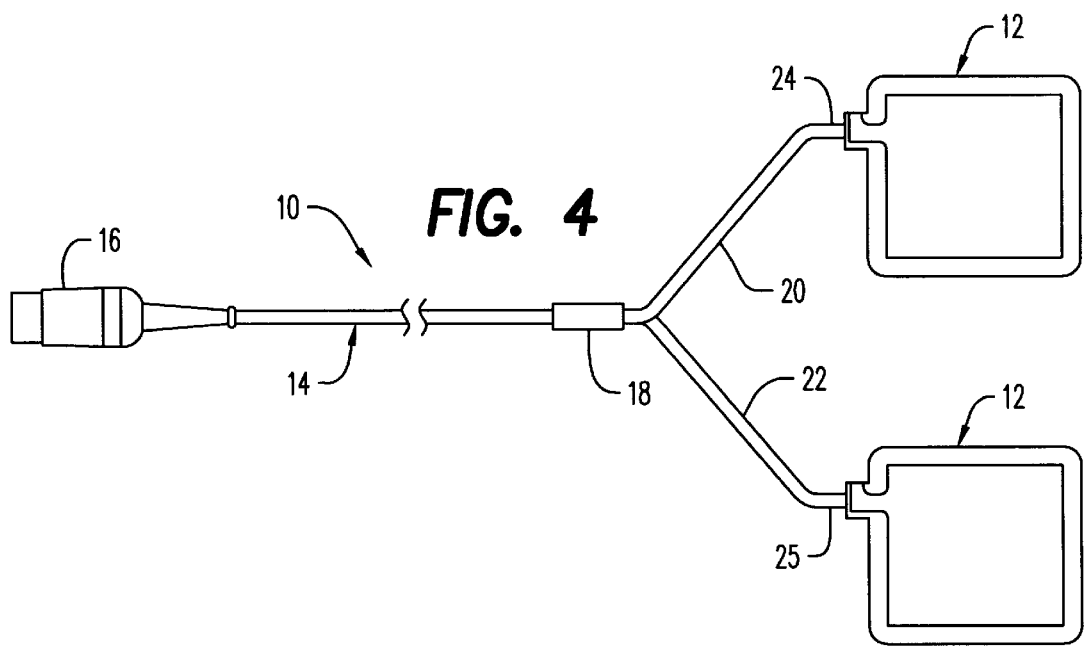
FIG. 4 is a top plan view of the invention.

Referring now additionally to FIGS. 4 to 8, the invention is shown generally at numeral 10 in FIG. 4 in its entirety. A total of up to four of these assemblies 10 may be used in conjunction with the control module A described hereabove. Each of the assemblies 10 include a multi-pin connector 16 which operably engages into any one of the output terminals E of control module A. Each of these assemblies 10 also includes a conduit harness shown generally at 14 and two separate multi-layered pads shown generally at numeral 12. These pads 12 are electrically connected by harness legs 20 and 22 through wiring splitter 18 to the input plug 16.

Figure 7:
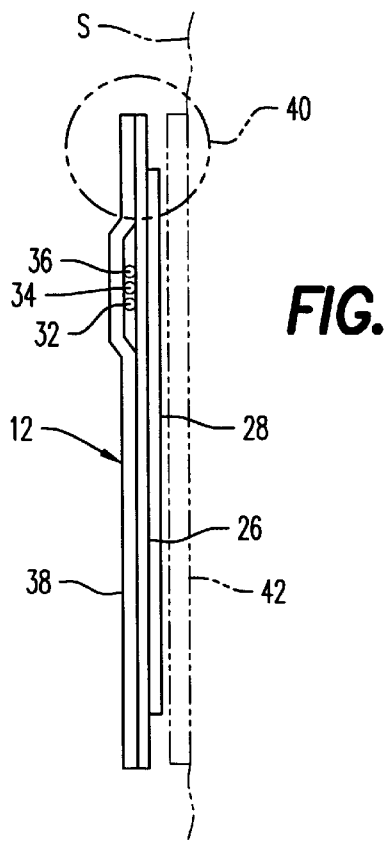
FIG. 7 is a left side elevation view of FIG. 5.
Figure 8:
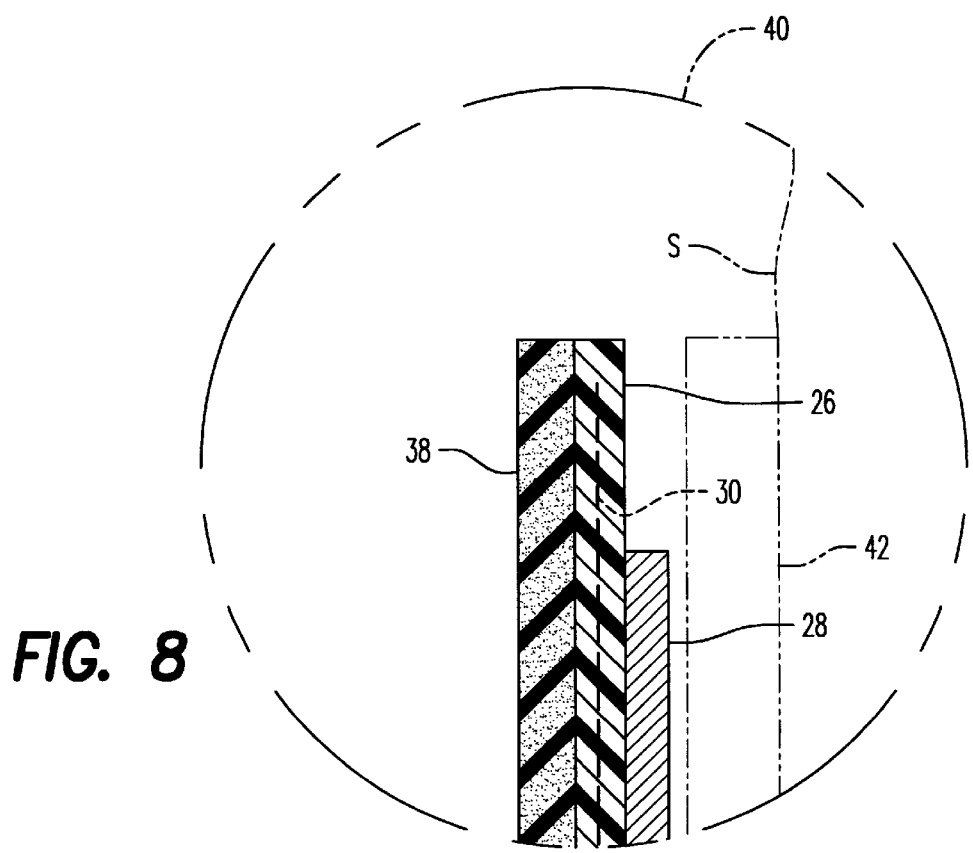
FIG. 8 is an enlarged view of area 40 of FIG. 7.

Each of the pads 12 includes a very thin foil layer 28 which is electrically conductive and which forms a working surface against which each of the pads 12 is interconnected to a double-sided adhesive electrode shown in phantom at 42 in FIGS. 7 and 8. These electrodes 42 are commercially available from LecTec Corporation of Minnetonka, Minn. under the product designation LT 4000 Hydrogel electrodes. These commercially available hydrogel electrodes 42 are highly adhesive and flexible so as to vigorously attach to both the skin of the patient and to the foil layer 28. The thickness of the foil layer 28 is in the range of 0.027".

Each pad 12 also includes a thin, flexible non-conductive heating layer 26 which is adhered directly against the opposite or concealed surface of each foil layer 28. Each heating layer 26 includes a conductive KAPTON heating element 30 which is embedded within the non-conductive heating layer 26 and is thusly electrically spaced from the foil layer 28. These heating elements 30 are commercially available from Minco Product, Inc., of Minneapolis, Minn. Each of these heating elements 30 has a thickness of about 0.04" and specifically custom fabricated to have a non-inductive heater element pattern with the resistance of 310 ohms and a rating of 4.9 watts at 39 volts d.c. input.

A protective insulating neoprene cover 38 is permanently adhered to the opposite surface of the heater layer 26 from the foil backing 28 so as to protectively conceal the KAPTON heating element 30 embedded within each heating layer 26. The neoprene cover 38 has a thickness of approximately 0.06" and is coextensive with the heater layer 26.

Figure 5:
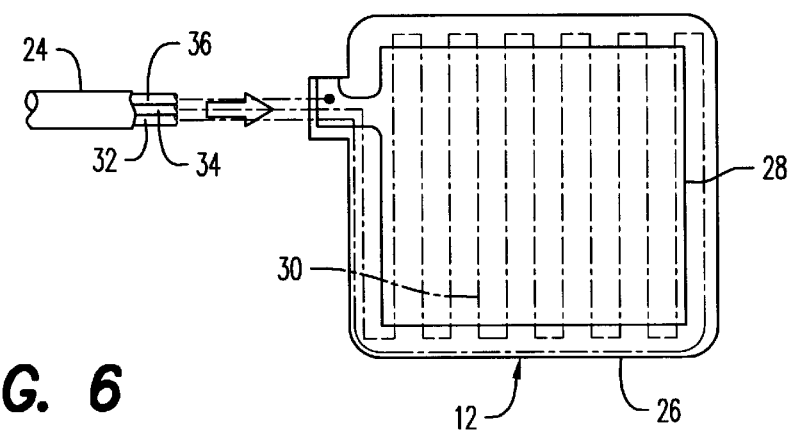
FIG. 5 is an enlarged broken view of one pad of FIG. 4.
Figure 6:
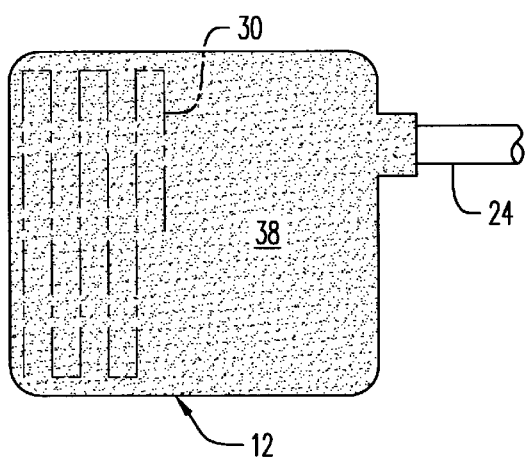
FIG. 6 is a bottom plan view of FIG. 5.

The wiring arrangement of the invention 10 is somewhat unique with respect to the flow of current stimulating the skin S and the soft body tissue beneath each of the pads 12 and therebetween. Each of the KAPTON heating elements 30 are individually wired at each end thereof to feed and return wires 32 and 34, respectively, within each lead 24 and 25 as best seen in FIG. 5. By this arrangement, current will flow through each of the elements and then return therefrom directly to the control module A.

However, one of the foil backing layers 28 is interconnected to a positive lead 36 from one leg of a separate suitable voltage and current power source within module A, while the other foil element from lead 25 (concealed) connects the other foil backing layer 28 to the return or ground leg of the power source providing electro-muscle stimulation current and voltage. By this arrangement, each muscle stimulation wiring conduit extending from connector 16 and split at 18 into two separate leads 20 and 22, establish a cooperating pair of pads 12 as shown in FIG. 4. Each of the foil backing layers 28 of each pad 12 of each pair of pads being operably connected to the distal ends of leads 20 and 22, the muscle stimulation current will flow from one of the foil backing members 28 of one pad 12 to the other backing member 28 of the other pad 12 of the pair and through skin S and soft tissue therebetween.

STIMULATOR CHARACTERISTICS

The pulse rate and intensity are settable on the controller by dual function keys C. In the muscle stimulator mode, the pulse rate may be varied between 1 and 150 pulses per second. The stimulator pulses for five seconds and then is off for five seconds.

The pulse width of the biphasic pulses may range from 1 to 415 microseconds according to the "intensity" setting. The second of the biphasic pair of pulses follows the first by 1 millisecond. The number of pulses per second may be adjusted from 1 to 150 by adjusting a potentiometer on the back of the controller box.

The interferential mode produces a triangular modulated stimulation waveform with a nominal pulse rate of 4000 Hz. The maximum intensity and the modulation rate may be adjusted on the controller. The modulation frequency can range from 1 to 150 Hz by adjusting the potentiometer on the back of the controller box. In this mode, electrodes are used in pairs.

A further unique feature of this arrangement is that the leads 20 and 22 may be established to a specific length, e.g. 8", so as to maximize the allowable spacing distance between each of the pair of pads 12 based upon the total desired available muscle stimulation current as programmed into the control module circuit in Figure A previously generally described.

While the instant invention has been shown and described herein in what are conceived to be the most practical and preferred embodiments, it is recognized that departures may be made therefrom within the scope of the invention, which is therefore not to be limited to the details disclosed herein, but is to be afforded the full scope of the claims so as to embrace any and all equivalent apparatus and articles.

What is claimed is:

1. A combination soft body tissue stimulator and heating device comprising:

a pair of thin, flat flexible pads each having one side thereof defining an electrically conductive working surface adapted for adhesive attachment to a thin disposable double-sided adhesive electrode adapted to be adhesively attached to a skin area over soft body tissue;

a resistive heating element embedded in each said pad electrically spaced from, and generally coextensive with, said working surface for heating each said pad;

first means for electrically connecting said working surface of one said pad to one leg of a source of pulsed electrical current and another said working surface of another said pad to a second leg of the source of pulsed electrical current for stimulating the soft body tissue;

second means for electrically connecting each said resistive heating element to a source of electric power for producing heat.

2. The combination soft body tissue stimulator and heating device as set forth in claim 1, wherein:

said first means is sized in length for limiting a maximum operational spacing between said pads with respect to the pulsed electrical current passing between said working surfaces and the skin areas and soft body tissue therebetween.

3. A combination soft body tissue stimulator and heating device comprising:

a pair of flexible unitary multi-layered pads each having one side thereof defining a conductive working surface;

a pair of thin disposable double-sided adhesive electrodes each having one side thereof adhesively attachable to one said working surface, another side of each said electrode adapted for adhesive attachment onto a skin area over a soft tissue;

each said pad including a resistive heating element electrically spaced from said working surface for heating said pad;

first means for electrically connecting one said working surface to one output terminal of a source of pulsed electrical current and another said working surface to another output terminal of the source of pulsed electrical current for stimulating the soft body tissue;

second means for electrically connecting each said resistive heating element to a source of electric power for heating the soft body tissue.

4. The combination soft body tissue stimulator and heating device as set forth in claim 3, wherein:

said first means is sized in length for limiting a maximum operational spacing between said pads with respect to the pulsed electrical current passing between said working surfaces and the skin areas and soft body tissue therebetween.

5. A combination soft body tissue stimulator and heating device comprising:

a flat flexible pair of pads each including one layer thereof defining a conductive working surface adapted for adhesive attachment to a thin disposable double-sided adhesive electrode, the electrode adapted to be attached to a skin area over a soft body tissue;

a resistive heating element of each said pad electrically spaced from said working surface for heating the soft body tissue;

first means for connecting each said working surface to a different polarity of a source of pulsed electrical current whereby the pulsed current will flow from one working surface to another said working surface through and stimulating the soft body tissue therebetween;

second means for connecting each said resistive heating element to a source of electric power for heating the soft body tissue.

6. The combination soft body tissue stimulator and heating device as set forth in claim 5, wherein:

said first means is sized in length for limiting a maximum operational spacing between said pads with respect to the pulsed electrical current passing between said working surfaces and the skin areas and soft body tissue therebetween.

* * * * *